March 22, 1955 C. H. CHRIST Plant Pat. 1,365
STRAWBERRY PLANT
Filed July 27, 1954
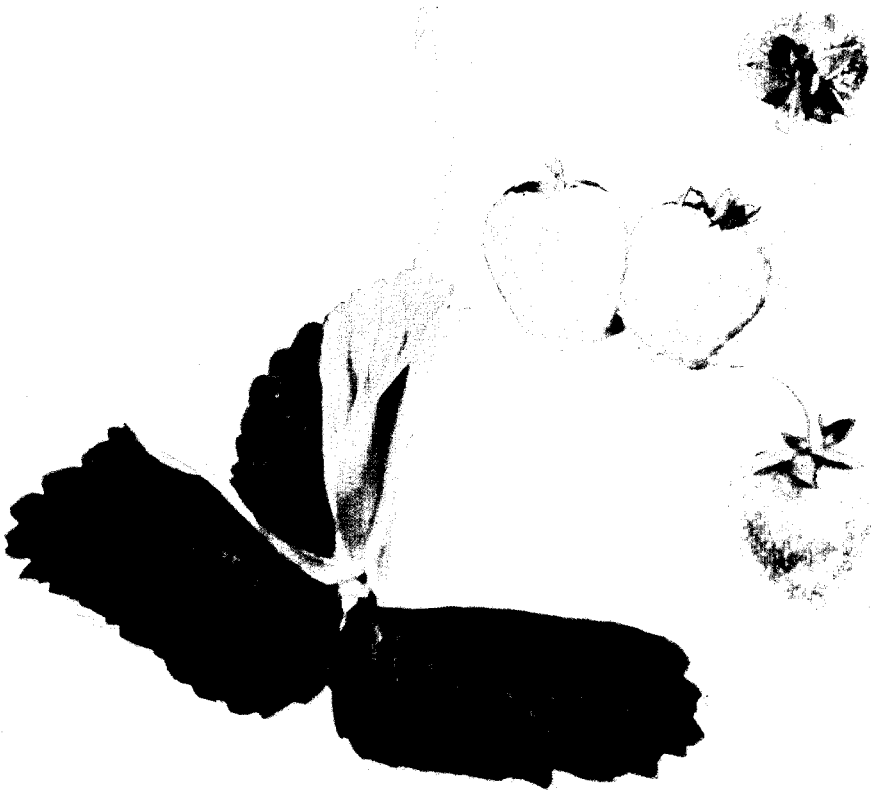
Inventor.
Clarence H. Christ
By: Robb & Robb
Attorneys.

United States Patent Office

Plant Pat. 1,365

Patented Mar. 22, 1955

1,365

STRAWBERRY PLANT

Clarence H. Christ, Arnold, Mo., assignor to Stark Bro's Nurseries and Orchards Company, Louisiana, Mo., a corporation of Missouri Application July 27, 1954, Serial No. 446,187

1 Claim. (Cl. 47—62)

The present invention relates to a new and distinct variety of strawberry plant which was originated by me by crossing the variety "Midland" (unpatented) with the variety "Fairpeak" (unpatented).

As the result of this cross, I have produced a new variety of strawberry plant which is particularly characterized as to novelty by the following characteristics:

(1) The new variety resembles "Bellmar" (unpatented) more than either parent or any other variety, but it is distinctly different from "Bellmar," as well as from all other strawberry varieties of which I am aware;

(2) The plants of the new variety are vigorous and very productive;

(3) The foliage has a superior resistance to leaf spot caused by *Mycosphaerella fragariae*; and (4) The fruit is relatively large, rounded, firm, and of a dark red color, said fruit being borne on relatively upright and long fruiting stems, and having a superior and rich flavor, with the dark red color of the fruit extending throughout both the skin and the flesh when fully ripe.

Asexual reproduction of my new variety by runners, as performed in Jefferson County, Missouri, shows that the foregoing characteristics and distinctions come true to form and are established and transmitted through succeeding propagations.

The accompanying drawing shows typical specimens of the fruit and foliage of my new variety as depicted in color as nearly true as it is reasonably possible to make the same in a color illustration of this character, with the fruit specimens shown in elevation, in plan, and in axial cross-section.

The following is a detailed description of my new variety, with color terminology in accordance with the Horticultural Colour Guide (hereinafter abbreviated as "H. C. G.") and Ridgway's Color Standards and Nomenclature (hereinafter abbreviated as "Ridgway"), as indicated, except where general color terms of ordinary dictionary significance are obvious:

Location where grown and observed: Jefferson County, Missouri.

Dates of first and last picking: May 14th to May 30th.

Plant:

*Growth.*—Vigorous.

*Root.*—Vigorous.

*Crown.*—Branched; large.

*Leaves.*—Many; large; central leaflet blade exceeds lateral.

Petiole: Long; stout; petiole of central leaflet equals ⅓ longer than that of the lateral.

Color: Spinach Green, Plate o960, page 187, vol. 2 (H. C. G.); with bracts.

Pubescence: Abundant on petiole; spreading; wanting on leaf surface, but medium on leaf veins.

Groove: Deep.

Serrations: Irregular; broadly ovated; ciliate on margin; apex tinged with Red about ¾ of margin of central leaflet and around upper ¾ of margin of lateral leaflets.

Leaflet surface: Upper — glossy; wrinkled, Color—Spinach Green, Plate o960, page 187, vol. 2 (H. C. G.). Lower—color—Spinach Green, Plate o960/3, page 187, vol. 2 (H. C. G.).

*Runners.*—Appear during fruiting; numerous; medium stocky.

*Flower stems.*—Long; inflorescence exposed.

Bloom: Medium late.

*Date first bloom.*—About April 12th.

*Date full bloom.*—About April 26th.

*Flowers.*—Many; perfect.

Breadth: Primary—1¼ inches; secondary—1⅛ inches.

Filaments of stamens: Medium long.

Pollen: Abundant.

Fruiting stems: Medium long; stout; upright.

*Radical.*—Shorter than main truss.

*Branches of truss.*—Few.

Soil where grown: Loamy; well-drained.

Culture: Mulched with straw; sprayed with "Orthocide 406."

Disease resistance: Good resistance to leaf spot caused by *Mycosphaerella fragariae*, as determined by comparison with other varieties grown under comparable cultural conditions in Jefferson County, Missouri.

Fruit: Ripens about 6 days later than "Bellmar."

*Condition when described.*—Prime.

*Date described.*—May 20th.

*Size.*—Variable, but relatively large; decreases late in season.

Average length: 1½ inches.

Average breadth: 1⅝ inches.

Average thickness: 1⅜ inches.

*Form.*—Uniform; regular; conical; necked; apex rounded.

*Stems.* — Radical — medium stout; short. Main truss—stout; long. Pubescence—abundant; reflexed.

*Calyx.*—Green after picking; even with surface; tenacious; large.

Upper surface: Color—Lettuce Green, Plate 861, page 176, vol. 2 (H. C. G.). Pubescence—abundant.

Lower surface: Color—Lettuce Green, Plate 861, page 176, vol. 2 (H. C. G.) at base, shading to Parsley Green, Plate oo962, page 193, vol. 2 (H. C. G.) at tips. Pubescence—scant.

Segments—8.

Length: 9/16 inch.

Breadth: ¼ inch.

Form: Oval; acute.

Epicalyx — present. Color: Upper surface—Lettuce Green, Plate 861, page 176, vol. 2 (H. C. G.); lower surface—Parsley Green, Plate oo962, page 193, vol. 2 (H. C. G.).

Segments—8.

Length: ½ inch.

Breadth: 3/16 inch.

Form: Narrowly oval; acute.

*Surface.* — Glossy. Color: Currant Red, Plate 822/1, page 168, vol. 2 (H. C. G.); few tips Pod Green, Plate o61/2, page 120, vol. 2 (H. C. G.).

Seeds: Conspicuous; even with surface; many large fertile lower seeds. Color—Light Green Yellow, Plate V, Colour No. 27, Tone *d* (Ridgway). Markings—none.

*Core.*—A few berries have hollow core. Color: Vermillion, Plate 18/1, page 18, vol. 1 (H. C. G.).

*Flesh.*—Juicy.

Color: Vermillion, Plate 18, page 18, vol. 1 (H. C. G.).

Texture: Firm; fine; crisp.

*Flavor.*—Subacid; rich; aromatic.

*Quality.*—Best. Shipping quality—good.

*Use.*—Market; canning; dessert.

I claim:

A new and distinct variety of strawberry plant, substantially as herein shown and described, characterized particularly as to novelty by its vigorous habit of growth and superior productivity, its large, rounded, firm fruit of Dark Red color borne on relatively upright and long fruiting stems, said fruit having a superior and rich subacid flavor, with the Dark Red color of the fruit extending throughout both the skin and the flesh when fully ripe, and the superior resistance of the foliage to leaf spot.

No references cited.